United States Patent
Gubbens et al.

(10) Patent No.: US 7,488,938 B1
(45) Date of Patent: Feb. 10, 2009

(54) CHARGE-CONTROL METHOD AND APPARATUS FOR ELECTRON BEAM IMAGING

(75) Inventors: Alexander Jozef Gubbens, Redwood City, CA (US); Mark Borowicz, San Jose, CA (US); Ye Yang, Fremont, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 232 days.

(21) Appl. No.: 11/509,137

(22) Filed: Aug. 23, 2006

(51) Int. Cl.
*G01N 23/00* (2006.01)
*H01J 37/20* (2006.01)
*H01J 37/22* (2006.01)
*H01J 37/28* (2006.01)

(52) U.S. Cl. .............. 250/310; 250/306; 250/307; 250/309; 250/311; 324/751; 324/765

(58) Field of Classification Search ......... 250/306, 250/307, 310, 311, 396 R, 398, 399, 492.1, 250/492.2, 492.3; 324/750, 751, 765
See application file for complete search history.

(56) References Cited

U.S. PATENT DOCUMENTS

| | | | |
|---|---|---|---|
| 3,458,752 A | | 7/1969 | Stowell |
| 4,415,851 A | | 11/1983 | Langner et al. |
| 5,045,705 A | | 9/1991 | Mollenstedt |
| 5,432,345 A | | 7/1995 | Kelly |
| 5,798,524 A | * | 8/1998 | Kundmann et al. ......... 250/305 |
| 5,973,323 A | | 10/1999 | Adler et al. |
| 5,986,263 A | * | 11/1999 | Hiroi et al. ............. 250/310 |
| 5,990,476 A | | 11/1999 | Larson et al. |
| 6,066,849 A | * | 5/2000 | Masnaghetti et al. ....... 250/310 |
| 6,091,249 A | * | 7/2000 | Talbot et al. ............ 324/751 |
| 6,172,365 B1 | * | 1/2001 | Hiroi et al. ............. 250/310 |
| 6,232,787 B1 | * | 5/2001 | Lo et al. ............... 324/751 |
| 6,252,412 B1 | | 6/2001 | Talbot et al. |
| 6,344,750 B1 | * | 2/2002 | Lo et al. ............... 324/751 |
| 6,465,781 B1 | | 10/2002 | Nishimura et al. |
| 6,566,897 B2 | * | 5/2003 | Lo et al. ............... 324/751 |
| 6,570,154 B1 | * | 5/2003 | Masnaghetti et al. ....... 250/310 |
| 6,586,736 B1 | * | 7/2003 | McCord ................. 250/310 |
| 6,734,429 B2 | | 5/2004 | Takagi |
| 6,765,205 B2 | | 7/2004 | Ochiai et al. |
| 6,781,669 B2 | * | 8/2004 | Tanaka ................. 355/53 |

(Continued)

OTHER PUBLICATIONS

McCord, M.A. "Use of Ultraviolet Light in charged Particle Systems to Reduce Charging and Contamination", IBM Technical Disclosure Bulletin, Pub. No. 10a, Mar. 1990, pp. 157-158, Yorktown, U.S.A.

*Primary Examiner*—Bernard E Souw
(74) *Attorney, Agent, or Firm*—Okamoto & Benedicto LLP (57) ABSTRACT

One embodiment relates to a method of electron beam imaging of a target area of a substrate. During an imaging phase, an electron beam is controllably scanned over the target area of the substrate, and extracted secondary electrons are detected. An electric field at a surface of the substrate is changed from an original electric field after the imaging phase. During a charge control phase, the electron beam is controllably scanned over the target area of the substrate. The electric field at the surface of the substrate is reverted back to the original electric field after the charge control phase. The imaging and charge control frames are interleaved. Other embodiments and features are also disclosed.

22 Claims, 4 Drawing Sheets

U.S. PATENT DOCUMENTS

| | | |
|---|---|---|
| 6,828,571 B1 | 12/2004 | McCord et al. |
| 6,930,308 B1 * | 8/2005 | Lorusso et al. ............... 250/310 |
| 6,930,309 B1 | 8/2005 | Mankos et al. |
| 7,019,294 B2 * | 3/2006 | Koyama et al. ............. 250/311 |
| 7,183,546 B2 * | 2/2007 | Bullock ...................... 250/310 |
| 7,230,240 B2 * | 6/2007 | Siebert et al. ............... 250/306 |
| 7,253,410 B1 * | 8/2007 | Bertsche et al. ............. 250/310 |
| 7,276,693 B2 * | 10/2007 | Koyama et al. ............. 250/310 |
| 2002/0130260 A1 | 9/2002 | McCord et al. |
| 2003/0141451 A1 | 7/2003 | Sato et al. |
| 2005/0023486 A1 | 2/2005 | Takakuwa et al. |
| 2005/0045821 A1 * | 3/2005 | Noji et al. .................... 250/311 |
| 2006/0163480 A1 * | 7/2006 | Koyama et al. ............. 250/310 |
| 2006/0169900 A1 * | 8/2006 | Noji et al. .................... 250/310 |
| 2007/0040118 A1 * | 2/2007 | Cheng et al. ................ 250/310 |

* cited by examiner

FIG. 4

CHARGE-CONTROL METHOD AND APPARATUS FOR ELECTRON BEAM IMAGING

BACKGROUND OF THE INVENTION

1. Field of the Invention

The present invention relates generally to electron beam imaging apparatus and methods of using same.

2. Description of the Background Art

Automated inspection and review systems are important in process control and yield management for the semiconductor and related microelectronics industries. Such systems include optical and electron beam (e-beam) based systems.

In the manufacture of semiconductor devices, detection of defects early on in the development and fabrication process is becoming increasingly important to shorten product development cycles and increase manufacturing yield. Advanced wafer inspection and review systems based on scanning electron microscopy technology are being used to detect, review and classify defects and feed the root cause information back into the manufacturing process to prevent these defects going forward. The size of relevant defects is directly proportional to the design rule being applied to the manufacturing of the semiconductor devices. As the latter continues to shrink the performance demands on wafer inspection and review SEMs increases both in terms of imaging resolution, elemental analysis capabilities, and speed (defects processed per hour).

With the decreasing size of defects, resolution limiting effects such as charging of the wafer surface become increasingly more performance limiting. Focus, distortion and contrast variations caused by uneven charge distribution can make e-beam inspection, review and classification unstable or even impossible. In order to successfully inspect and review a wafer it is therefore highly advantageous to be able to control any surface charging.

It is desirable to improve e-beam inspection and review apparatus. In particular, it is desirable to better control effects of charging and discharging on images used for inspection and review.

DETAILED DESCRIPTION

In a conventional scanning electron microscope, a beam of primary electrons is scanned over a sample (for example, a semiconductor wafer) in the form of multiple raster and/or line scans. The primary electrons scatter in the sample causing secondary and backscattered electrons to be emitted that are then detected by a detector that is coupled with a computer system. The computer system transforms the detected signal into an image that is stored and/or displayed on the computer system.

Conventional scanning electron microscopy systems and techniques typically produce images having an adequate level of quality on non-insulating samples, but they tend to produce poor quality images on insulating samples.

The total number of emitted secondary and backscattered electrons per incoming primary electron varies with (among others) the landing energy and the material in the sample. In most cases the yield is either smaller or bigger than one outgoing electron per one incoming electron and a net current flows in or out of the surface of the sample. In the case of insulators this current cannot be compensated by an equivalent current flowing through the bulk, causing the surface to charge up and its potential to change. The characteristics of the charging depend strongly on the local environment. Neighboring structures and materials in the sample may have different secondary and backscattered electron yields, and different levels of conductivity, and therefore give rise to varying potentials across the surface. The resulting local electric fields can be quite strong and affect the focusing and scan position of the primary beam as well as the collection efficiency of the secondary and backscattered electrons. The net result is a variation in focus, distortion, and shading across the field of view. Excessive charging can completely overwhelm the regular signal contrast and make defects undetectable. It can also lead to electric discharges and catastrophic damage.

The level of charging is affected by the presence of an electric field between the sample and its surroundings; for instance between the sample and the objective lens above it. An extracting electric field will accelerate the secondary and backscattered electrons away from the sample, increase their net yield, and so cause the charging to become more positive. A suppressing electric field will decelerate the secondary and backscattered electrons, decrease their net yield, and so cause the charging to become more negative.

Modern low voltage SEMs often use strong accelerating electric fields ranging from hundreds to thousands of volts per millimeter at the wafer in order to minimize their optical aberrations. While this optimizes their resolution performance, it also exacerbates the charging of the sample as per the argument above. On some samples this prevents the SEM's full resolution potential from being realized.

Several solutions to control or mitigate the effects of charging in SEMs have been suggested and implemented. One solution is to flood the sample with either positively or negatively charged particles at a time separate from the imaging of the sample. The intent of using such flooding is to equalize the charge levels across the sample, thus improving the focus, distortion and contrast uniformity of the images.

For example, conventional electron beam imaging apparatus commonly use a separate flood gun for charge control. This flood gun is separate from the electron gun for the primary (imaging) electron beam. The use of such a flood gun to control charging is discussed below in relation to FIG. 1.

Figure 1:
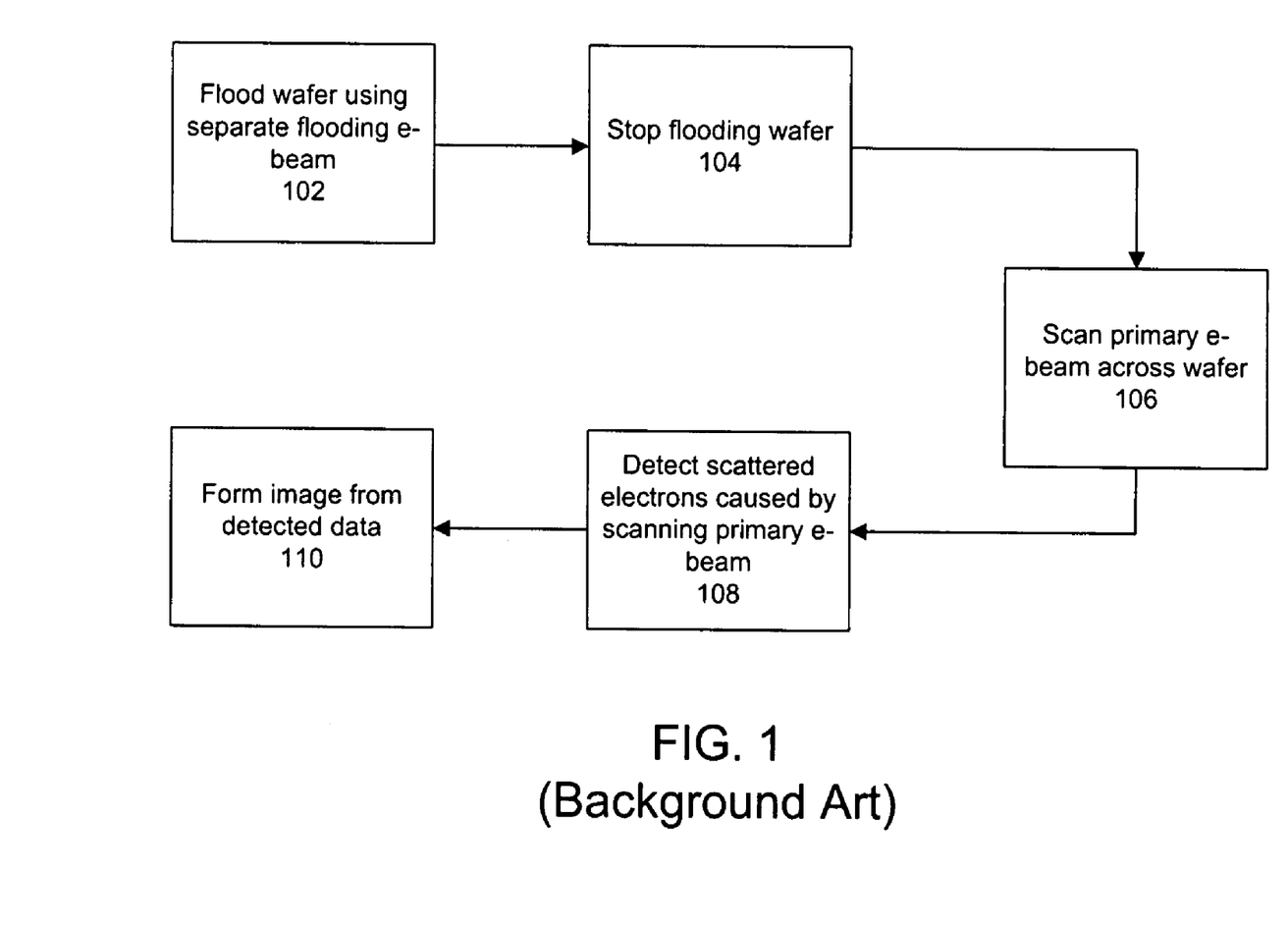
FIG. 1 is a flow chart of a conventional method of pre-flooding with a separate e-beam and subsequently imaging the wafer with a primary e-beam.

FIG. 1 is a flow chart of a conventional method of pre-flooding with a separate e-beam and subsequently imaging the wafer with a primary e-beam. In this conventional technique, before imaging, the wafer is flooded 102 with electrons using the separate flooding e-beam. This flooding 102 is applied for a period of time sufficient to control a charge level at the wafer. Thereafter, the electron flooding 102 of the wafer is stopped 104, and the imaging of the wafer is begun. The primary e-beam is scanned 106 across the wafer, and scattered (secondary and/or backscattered) electrons are detected 108. An image is formed 110 from the detected data. In some cases, several scans 106 may be used and the data may be averaged.

In an alternate arrangement the flooding beam is generated by the primary inspection or review column itself. Beam parameters such as beam current, and landing energy may be varied to most optimally mitigate the charging.

The present application discloses a technique of charge-control for electron beam (e-beam) imaging. Other techniques relating to charge-control for e-beam imaging are disclosed in commonly-assigned U.S. patent application Ser. Nos. 10/699,708 ("Apparatus and Methods of Controlling Surface Charge and Focus," filed Nov. 3, 2003, now issued at U.S. Pat. No. 6,828,571), 10/942,184 ("Method of Charging Substrate to a Potential," filed Sep. 16, 2004), 11/225,917 ("Charge-Control Pre-Scanning for E-Beam Imaging," filed Sep. 13, 2005) and 11/077,519 ("Sample Charging Control in Charged-Particle Systems," filed Mar. 10, 2005).

The present disclosure centers on a modulation of an electric field at the sample. If a sample charges positively during an imaging phase, then the sample can be guaranteed to charge negatively during a charge control phase by applying a suppressing electric field sufficiently strong to prevent any secondary and/or backscattered electrons from escaping. The net outflow of electrons in the imaging phase is now replaced by a net inflow during the charge control phase. If properly balanced, the negative and positive charging patterns cancel each other and the sample can be held at a low average charging pattern. The balancing can be done through a control of the magnitude of the suppressing electric field in combination with the relative duration of the imaging and charge control phases, and/or the relative beam currents during the imaging and charge control phases, and/or the landing energy during the imaging and charge control phases.

Similarly for a sample that charges negatively during an imaging phase, the sample may be able to be made to charge positively during a charge control phase by applying an accelerating electric field that increase the net secondary and backscattered electron yield. The net inflow of electrons in the imaging phase is now replaced by a net outflow during the charge control phase. If properly balanced, the negative and positive charging patterns cancel each other and the sample can be held at a low average charging pattern. The balancing can be done through a control of the magnitude of the accelerating electric field in combination with the relative duration of the imaging and charge control phases, and/or the relative beam currents during the imaging and charge control phases, and/or the landing energy during the imaging and charge control phases.

Whereas the first method guarantees negative charging during the charge control phase, the second method will only result in positive charging for a range of sample and operation conditions.

It should be understood that the application above of a suppressing electric field during the charge control phase can in fact mean the strengthening of a suppressing field that was already present during the imaging phase. Similarly the application above of an accelerating electric field during the charge control phase can in fact mean the strengthening of an accelerating field that was already present during the imaging phase.

Figure 2:
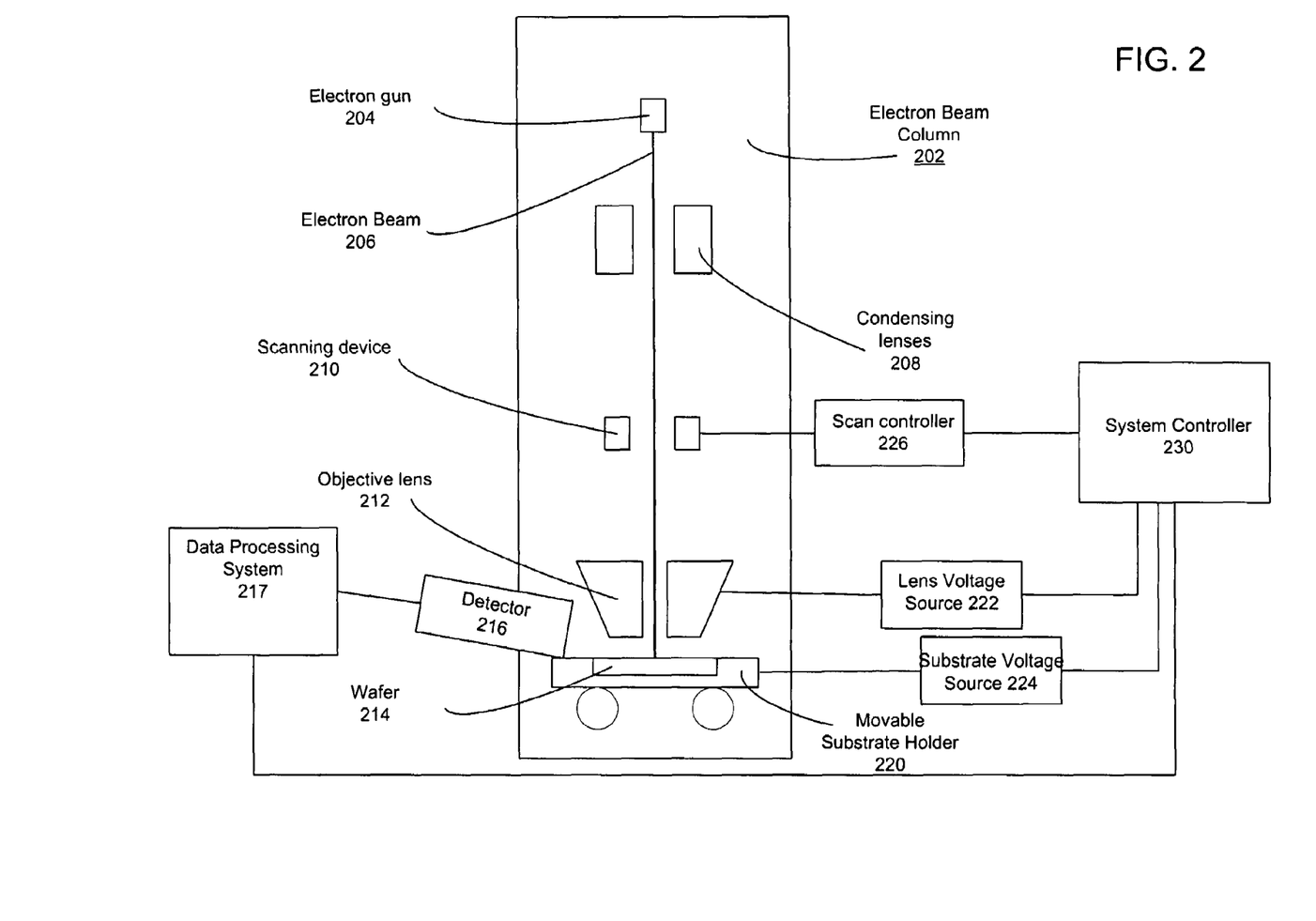
FIG. 2 is a schematic diagram of an electron beam imaging apparatus in accordance with an embodiment of the invention.

FIG. 2 is a schematic diagram of an electron beam imaging apparatus in accordance with an embodiment of the invention. As shown, the apparatus includes an electron beam column 202.

The electron beam column 202 includes an electron gun 204 that is the source of electrons for the incident electron beam 206. The gun lens in combination with condenser lenses 208 and a beam limiting aperture (not shown) control the beam current and set the beam 206 up to be focused by the objective lens 212.

The beam 206 is controllably deflected using scanning device 210 so as to scan the beam across the desired area. A scan controller 226 may be coupled to the scanning device 210 and used to control said deflection.

An objective lens 212 focuses the controllably deflected beam onto the semiconductor wafer (or other substrate) 214. A substrate holder 220 holds the wafer 214 and may be configured to transport (move) wafer under the imaging column 202 for the purpose of automated inspection and/or review of defects during the manufacturing process as circuits are manufactured on the semiconductor wafer 214.

A detector 216 is arranged to detect secondary electrons (and/or backscattered electrons). A data processing system 217 coupled to the detector 216 is used to store and process the detected data so as to be able to form useful images for analysis.

In accordance with an embodiment of the invention, the apparatus includes a lens voltage source 222 which is conductively coupled to the objective lens 212. The lens voltage source 222 produces an electrical voltage which is applied to the objective lens 212 and used to control the voltage at the objective lens 212.

The apparatus further includes a substrate voltage source 224 which is conductively coupled to the substrate holder 220. The substrate voltage source 224 produces an electrical voltage which is applied to the substrate holder 220 and used to control the voltage at the wafer (or other substrate) 214.

The apparatus further includes a system controller 220. The system controller 220 may include a processor, memory for executable instructions and data, and various other components. The system controller 230 may be communicatively coupled to the scan controller 226, the lens voltage source 222, the substrate voltage source 224, and the data processing system 217.

Figure 3:
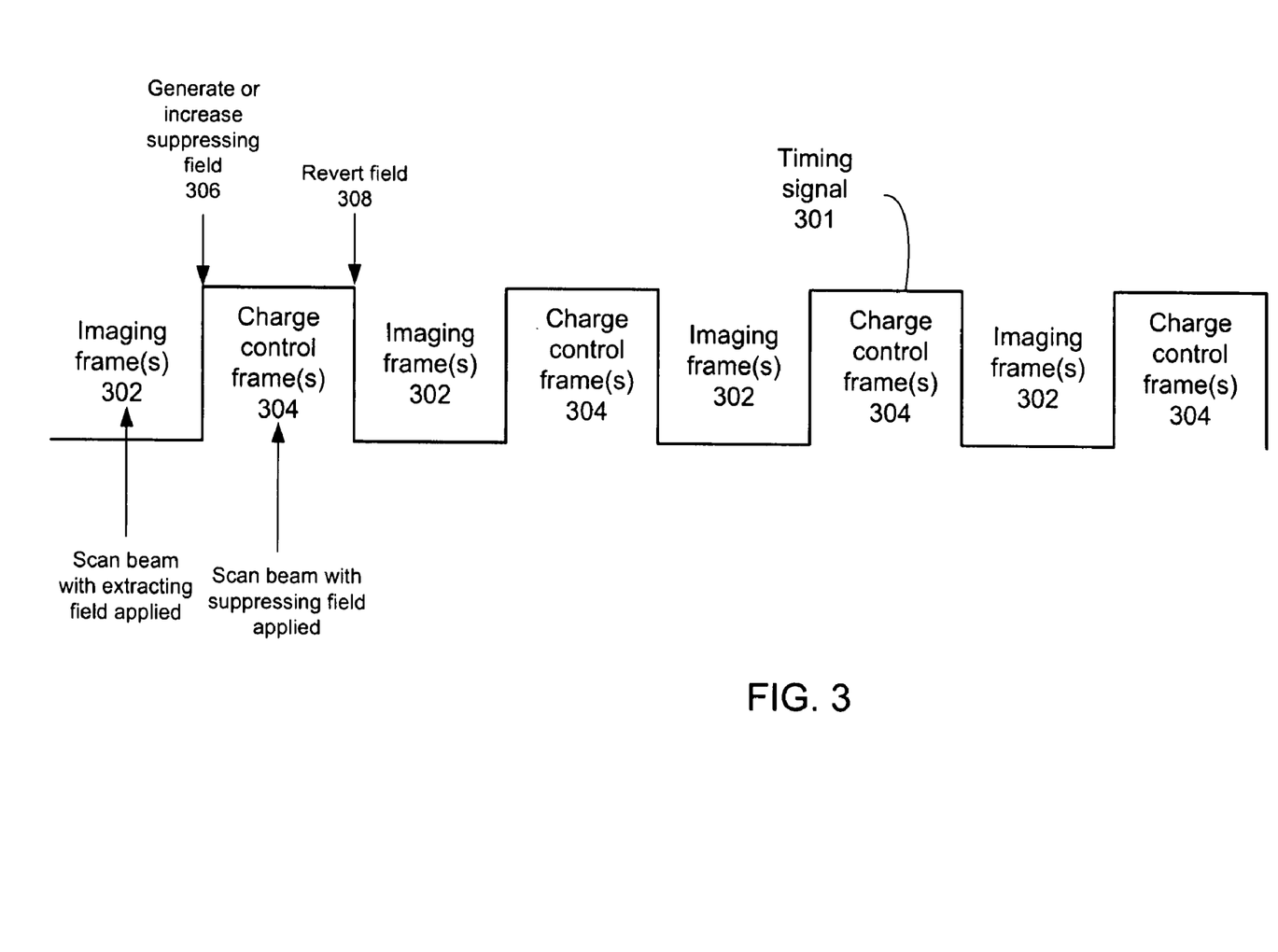
FIG. 3 is a timing diagram illustrating a method of charge control for electron beam imaging in accordance with an embodiment of the invention.

FIG. 3 is a timing diagram illustrating a method of charge control for electron beam imaging in accordance with an embodiment of the invention. An example timing signal 301 is depicted, where each cycle of the timing signal 301 includes two phases. The first phase corresponds to one or more imaging frames 302, and the second phase corresponds to one or more charge control frames 304. The diagram shows an example where the durations of the first and second phases are the same. However, in an alternate embodiment, the duration of the two phases may be varied, for example, by changing the duty cycle of the timing signal 301.

In an embodiment of the invention, the timing signal 301 has a frequency of fifteen hertz or more. In other words, each second would include at least fifteen imaging phases 302 and fifteen charge control phases 304 interleaved therewith.

During the imaging phase 302, the electron beam 206 is controllably deflected so as to scan the beam 206 over an area of the wafer 214. Also during each imaging frame 302, an extracting electric field may be applied to the surface of the wafer 214. In one implementation, the extracting field is applied by controlling a lens voltage source 222 and a substrate voltage source 224. The voltage sources are controlled so that the lens 212 is at a higher voltage than the wafer 214, such that an electric field pointing towards the surface of the wafer 214 is created. Because electrons have negative charge, such an electric field acts as an extracting field.

During the charge control phase 304, the electron beam 206 is also controllably deflected so as to scan the beam 206 over an area of the wafer 214. In addition, during the charge control phase 304, a suppressing electric field may be applied to the surface of the wafer 214. In one implementation, the suppressing field is applied by controlling a lens voltage source 222 and a substrate voltage source 224. The voltage sources are controlled so that the lens 212 is at a lower voltage than the wafer 214, such that an electric field pointing away from the surface of the wafer 214 is created. Because electrons have negative charge, such an electric field acts as a suppressing field. As a result of the suppressing field, secondary and/or backscattered electrons are suppressed so as to return to the wafer 214. This provides negative charging to compensate for prior positive charging of the wafer 214. For example, if the imaging phase 302 results in positive charging of the wafer 214, then this may be mitigated (compensated for) by the negative charging during the following charge control phase 304.

After each imaging phase 302 (and before the following charge control phase 304), the electric field at the surface of the wafer 214 is reversed in polarity 306. This changes the extracting field to a suppressing field. For example, the voltage difference between the lens voltage source 222 and the substrate voltage source 224 may be reversed in polarity. The magnitude of the voltage difference may be the same after the polarity reversal 306 or may change. In one implementation, the polarity reversal 306 may be achieved by lowering the voltage output by the lens voltage source 222 so that it is negative relative to the sample potential. In another implementation, the polarity reversal 306 may be achieved by raising the voltage output by the substrate voltage source 224 so that it is positive relative to the potential at the objective lens. In another implementation, the polarity reversal 306 may be achieved by both lowering the voltage output by the lens voltage source 222 and raising the voltage output by the substrate voltage source 224.

Similarly, after each charge control phase 304 (and before the subsequent imaging phase 302), the electric field at the surface of the wafer 214 is reversed in polarity 308. This changes the suppressing field to an extracting field. For example, the voltage difference between the lens voltage source 222 and the substrate voltage source 224 may be reversed in polarity. The magnitude of the voltage difference may be the same after the polarity reversal or may change. In one implementation, the polarity reversal 308 may be achieved by raising the voltage output by the lens voltage source 222 so that it is positive relative to the sample potential. In another implementation, the polarity reversal 308 may be achieved by lowering the voltage output by the substrate voltage source 224 so that it is negative relative to the potential at the objective lens. In another implementation, the polarity reversal 308 may be achieved by both raising the voltage output by the lens voltage source 222 and lowering the voltage output by the substrate voltage source 224.

Preferably, the voltage difference between the objective lens 212 and the substrate holder 220 is changed by a magnitude not more than a few thousand volts, between imaging and charge control phases (during reversals 306 and 308 of the field).

Figure 4:
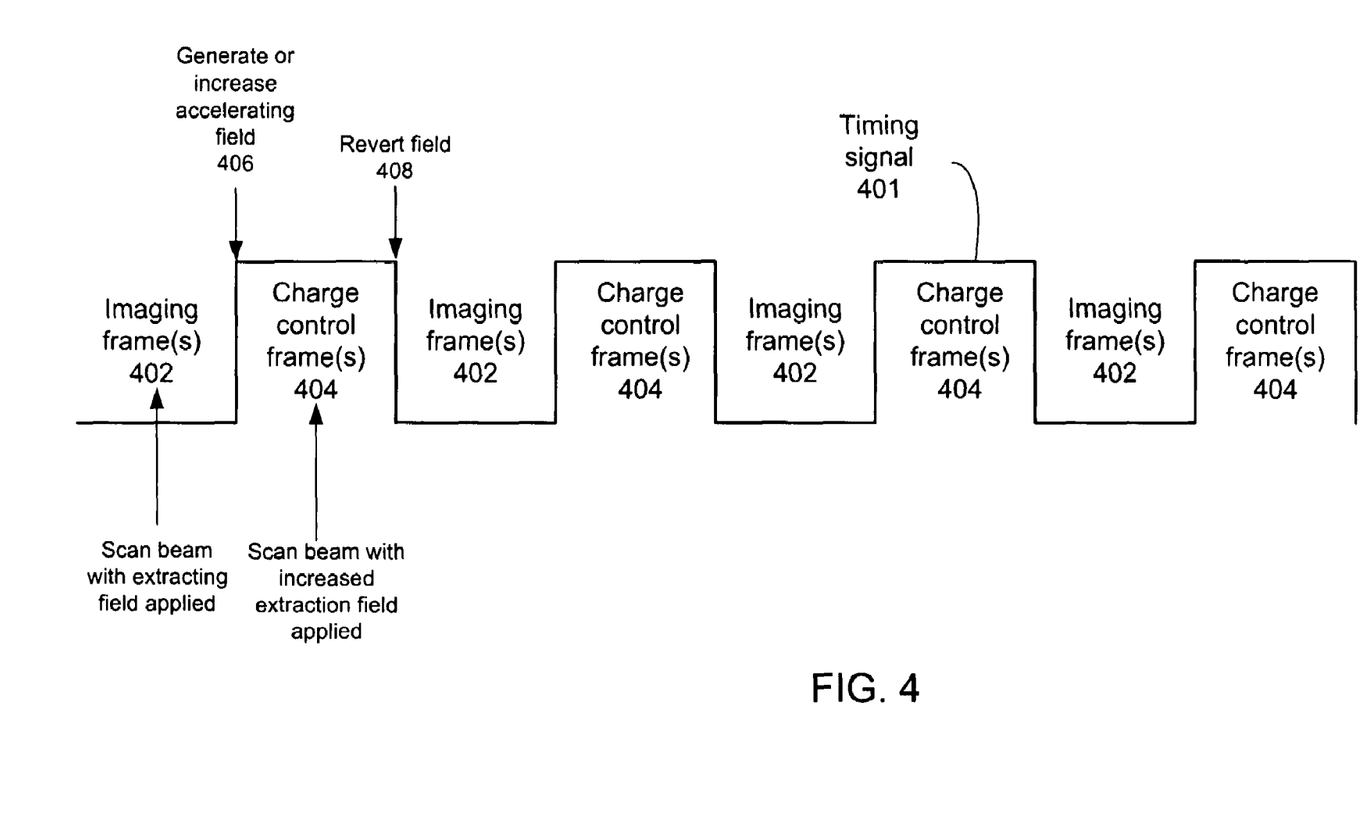
FIG. 4 is a timing diagram illustrating a method of charge control for electron beam imaging in accordance with an embodiment of the invention.

FIG. 4 is a timing diagram illustrating a method of charge control for electron beam imaging in accordance with an embodiment of the invention. An example timing signal 401 is depicted, where each cycle of the timing signal 401 includes two phases. The first phase corresponds to one or more imaging frames 402, and the second phase corresponds to one or more charge control frames 404. The diagram shows an example where the durations of the first and second phases are the same. However, in an alternate embodiment, the duration of the two phases may be varied, for example, by changing the duty cycle of the timing signal 401.

In an embodiment of the invention, the timing signal 401 has a frequency of fifteen hertz or more. In other words, each second would include at least fifteen imaging frames 402 and fifteen charge control frames 404 interleaved therewith.

During each imaging phase 402, the electron beam 206 is controllably deflected so as to scan the beam 206 over an area of the wafer 214. Also during each imaging frame 402, a lower-magnitude extracting electric field may be applied to the surface of the wafer 214. In one implementation, the lower-magnitude extracting field is applied by controlling a lens voltage source 222 and a substrate voltage source 224. The voltage sources are controlled so that the lens 212 is at a somewhat higher voltage than the wafer 214, such that a lower-magnitude electric field pointing towards the surface of the wafer 214 is created. As a result of the lower-magnitude extracting field, secondary and/or backscattered electrons are extracted from the wafer 214 so as to be detected by the detector 216.

During each charge control phase 404, the electron beam 206 is also controllably deflected so as to scan the beam 206 over an area of the wafer 214. In addition, during each charge control phase 404, a higher-magnitude extracting electric field may be applied to the surface of the wafer 214. In one implementation, the higher-magnitude extracting field is applied by controlling a lens voltage source 222 and a substrate voltage source 224. The voltage sources are controlled so that the lens 212 is at a substantially higher voltage than the wafer 214, such that a higher-magnitude electric field pointing towards the surface of the wafer 214 is created. As a result of the higher-magnitude field, an increased number of secondary and/or backscattered electrons escape from the wafer 214. This provides positive charging to compensate for prior negative charging of the wafer 214. For example, if the imaging phase 402 results negative charging of the wafer 214, then this may be mitigated (compensated for) by the positive charging during the following charge control phase 404.

After each imaging phase 402 (and before the following charge control frame 404), the electric field at the surface of the wafer 214 is increased 406. This changes the lower-magnitude extracting field to a higher-magnitude extracting field. For example, the voltage difference between the lens voltage source 222 and the substrate voltage source 224 may be increased. In one implementation, the voltage output by the lens voltage source 222 may be raised so as to be more positive relative to the sample potential. In another implementation, the voltage output by the substrate voltage source 224 may be lowered so as to be more negative relative to the potential at the objective lens. In another implementation, both the voltage output by the lens voltage source 222 may be raised and the voltage output by the substrate voltage source 224 may be lowered.

Similarly, after each charge control phase 404 (and before the subsequent imaging phase 402), the electric field at the surface of the wafer 214 is decreased 408. This changes the higher-magnitude extracting field to a lower-magnitude extracting field. For example, the voltage difference between the lens voltage source 222 and the substrate voltage source 224 may be decreased. This is preferably done by reversing the change or changes made to increase the voltage difference after each imaging frame 402.

Preferably, the voltage difference between the objective lens 212 and the substrate holder 220 is changed by a magnitude ranging up to a few thousand volts or more, between imaging and charge control frames (during the increase 406 and the decrease 408 in extracting field).

The above-described diagrams are not necessarily to scale and are intended be illustrative and not limiting to a particular implementation. The above-described invention may be used, for example, in an automatic inspection or review system and applied to the inspection or review of wafers, optical masks, X-ray masks, electron-beam-proximity masks and stencil masks and similar substrates in a production environment.

One embodiment of the invention relates to a method of electron beam imaging of a target area of a substrate using a sequence of imaging and charge control frames. During the imaging frame(s), an electron beam is controllably scanned over the target area of the substrate, and emitted secondary electrons and/or backscattered electrons are detected. After the imaging frame(s) the electric field is made more suppressing so that fewer secondary and/or backscattered electrons can escape from the wafer. During the following charge control frame(s), the electron beam is again controllably scanned over the target area of the substrate and the wafer will charge negatively. After the charge control frame(s) the electric field at the wafer is restored to that present during the imaging frame(s). The interleaved imaging and charge control frame (s) may be of different durations, the number of imaging and charge control frames need not be constant or equal, nor do their respective fields of view, probe currents, or landing energies need to be constant or equal. These parameters may be optimized to most effectively mitigate the charging.

Another embodiment of the invention relates to a method of electron beam imaging of a target area of a substrate using a sequence of imaging and charge control phases. During the imaging phase, an electron beam is controllably scanned over the target area of the substrate, and emitted secondary electrons and/or backscattered electrons are detected. After the imaging phase, the electric field is made more extracting so that more secondary and backscattered electrons can escape from the wafer. During the following charge control phase, the electron beam is again controllably scanned over the target area of the substrate and the wafer will charge positively. After the charge control phase the electric field at the wafer is restored to that present during the imaging phase The interleaved imaging and charge control phases may be of different durations, the number of imaging and charge control phases need not be constant or equal, nor do their respective fields of view, probe currents, or landing energies need to be constant or equal. These parameters may be optimized to most effectively mitigate the charging.

Another embodiment relates to an apparatus with an electron beam column for imaging a target area of a substrate. The apparatus includes an electron source configured to generate electrons for an electron beam, scanning deflectors configured to deflect the electron beam over the target area, an objective lens for focusing the electron beam onto the target area, a substrate holder for holding the substrate, a detector configured to detect scattered electrons, a controller configured to control the apparatus, and computer-readable program code stored in computer-readable data storage accessible by the controller. The computer-readable program code is configured to a) controllably scan an electron beam over the target area of the substrate and detect extracted secondary and/or backscattered electrons during an imaging phase, b) apply a more suppressing electric field at a surface of the substrate after the imaging phase, c) controllably scan the electron beam over the target area of the substrate during a charge control phase, and d) restore the original electric field at the surface of the substrate after the charge control phase. The imaging and charge control phases alternate.

Another embodiment relates to an apparatus with an electron beam column for imaging a target area of a substrate. The apparatus includes an electron source configured to generate electrons for an electron beam, scanning deflectors configured to deflect the electron beam over the target area, an objective lens for focusing the electron beam onto the target area, a substrate holder for holding the substrate, a detector configured to detect scattered electrons, a controller configured to control the apparatus, and computer-readable program code stored in computer-readable data storage accessible by the controller. The computer-readable program code is configured to a) controllably scan an electron beam over the target area of the substrate and detect extracted secondary and/or backscattered electrons during an imaging phase, b) apply a more extracting electric field at a surface of the substrate after the imaging phase, c) controllably scan the electron beam over the target area of the substrate during a charge control phase, and d) restore the original electric field at the surface of the substrate after the charge control phase. The imaging and charge control phases alternate.

In another embodiment, the image phase and the charge control phase may each comprise one or more swaths, instead of frames. To cover a swath, the stage holding the target substrate may be moved in one direction as the beam scans in an orthogonal direction.

In the above description, numerous specific details are given to provide a thorough understanding of embodiments of the invention. However, the above description of illustrated embodiments of the invention is not intended to be exhaustive or to limit the invention to the precise forms disclosed. One skilled in the relevant art will recognize that the invention can be practiced without one or more of the specific details, or with other methods, components, etc. For instance the apparatus in FIG. 2 may contain any number of lenses and any number of deflectors in any order. Any lens or deflector may be magnetic and/or electric. The detection of the secondary and/or backscattered electrons may occur outside and/or through the objective lens. The sample may or may not be immersed in the magnetic and/or electric field.

In other instances, well-known structures or operations are not shown or described in detail to avoid obscuring aspects of the invention. While specific embodiments of, and examples for, the invention are described herein for illustrative purposes, various equivalent modifications are possible within the scope of the invention, as those skilled in the relevant art will recognize.

These modifications can be made to the invention in light of the above detailed description. The terms used in the following claims should not be construed to limit the invention to the specific embodiments disclosed in the specification and the claims. Rather, the scope of the invention is to be determined by the following claims, which are to be construed in accordance with established doctrines of claim interpretation.

What is claimed is:

1. A method of electron beam imaging of a target area of a substrate, the method comprising:

controllably scanning an electron beam over the target area of the substrate and detecting extracted secondary electrons during an imaging phase including one or more imaging frames;

generating or increasing a suppressing electric field at a surface of the substrate from an original electric field to a more suppressing electric field after the imaging phase;

controllably scanning the electron beam over the target area of the substrate during a charge control phase including one or more charge control frames; and reverting the electric field at the surface of the substrate back to the original electric field after the charge control phase, wherein the imaging and charge control phases are interleaved.

2. The method of claim 1, wherein the generation or increase of the suppressing electric field at the surface of the substrate after the imaging phase is performed by lowering a voltage applied to an objective lens device, and wherein reverting the electric field at the surface of the substrate after the charge control phase is performed by raising the voltage applied to the objective lens device.

3. The method of claim 1, wherein the generation or increase of the suppressing electric field at the surface of the substrate after the imaging phase is performed by raising a voltage applied to a substrate holder device, and wherein reverting the electric field at the surface of the substrate after the charge control phase is performed by lowering the voltage applied to the substrate holder device.

4. The method of claim 1, wherein the generation or increase of the suppressing electric field at the surface of the substrate after the imaging phase is performed by both lowering a voltage applied to an objective lens device and raising a voltage applied to a substrate holder device, and wherein reverting the electric field at the surface of the substrate after the charge control phase is performed by both raising the voltage applied to the objective lens device and lowering the voltage applied to the substrate holder device.

5. The method of claim 1, wherein a voltage difference between an objective lens device and a substrate holding device is changed by at least a magnitude of one hundred volts between imaging and charge control phases.

6. The method of claim 1, wherein duration of the imaging phase is equal to duration of the charge control phase.

7. The method of claim 1, wherein duration of the imaging phase is different from duration of the charge control phase.

8. The method of claim 1, wherein a cycle including the imaging phase and the charge control phase is repeated at a frequency of at least fifteen hertz.

9. A method of electron beam imaging of a target area of a substrate, the method comprising:
controllably scanning an electron beam over the target area of the substrate and detecting extracted secondary and/or backscattered electrons during an imaging phase including one or more imaging frames;
generating or increasing an extracting electric field at a surface of the substrate after the imaging phase;
controllably scanning the electron beam over the target area of the substrate during a charge control phase including one or more charge control frames; and
reverting the extracting electric field at a surface of the substrate after the charge control phase,
wherein the imaging and charge control phases are interleaved.

10. The method of claim 9, wherein the generation or increase of the extracting electric field at the surface of the substrate after the imaging phase is performed by lowering a voltage applied to an objective lens device, and wherein the reversion of the extracting electric field at the surface of the substrate after the charge control phase is performed by raising the voltage applied to the objective lens device.

11. The method of claim 9, wherein the generation or increase of the extracting electric field at the surface of the substrate after the imaging phase is performed by raising a voltage applied to a substrate holder device, and wherein the reversion of the extracting electric field at the surface of the substrate after the charge control phase is performed by lowering the voltage applied to the substrate holder device.

12. The method of claim 9, wherein the generation or increase of the extracting electric field at the surface of the substrate after the imaging frames is performed by both lowering a voltage applied to an objective lens device and raising a voltage applied to a substrate holder device, and wherein the reversion of the extracting electric field at the surface of the substrate after the charge control frames is performed by both raising the voltage applied to the objective lens device and lowering the voltage applied to the substrate holder device.

13. The method of claim 9, wherein a voltage difference between an objective lens device and a substrate holding device is changed by at least a magnitude of one hundred volts between imaging and charge control phases.

14. The method of claim 9, wherein duration of the imaging phase is equal to duration of the charge control phase.

15. The method of claim 9, wherein duration of the imaging phase is different from duration of the charge control phase.

16. The method of claim 9, wherein a cycle including the imaging phase and the charge control phase is repeated at a frequency of at least fifteen hertz.

17. An apparatus with an electron beam column for imaging a target area of a substrate, the apparatus comprising:
an electron source configured to generate electrons for an electron beam;
scanning deflectors configured to deflect the electron beam over the target area;
an objective lens for focusing the electron beam onto the target area;
a substrate holder for holding the substrate;
a detector configured to detect scattered electrons;
a controller configured to control the apparatus; and
computer-readable program code stored in computer-readable data storage accessible by the controller, wherein the computer-readable program code is configured to a) controllably scan an electron beam over the target area of the substrate and detect extracted secondary and/or backscattered electrons during an imaging phase, b) change an electric field at a surface of the substrate after the imaging phase, c) controllably scan the electron beam over the target area of the substrate during a charge control phase, and d) revert the electric field at the surface of the substrate after the charge control phase, wherein the imaging and charge control phases alternate.

18. The apparatus of claim 17, wherein a voltage difference between the objective lens device and the substrate holder is changed by at least a magnitude of one hundred volts between imaging and charge control phases, and wherein a cycle including the imaging phase and the charge control phase is repeated at a frequency of at least fifteen hertz.

19. The apparatus of claim 17, wherein the substrate is controllably moved in a direction perpendicular to a scan direction so that the electron beam is scanned over swaths during the alternating imaging and charge control phases.

20. An apparatus with an electron beam column for imaging a target area of a substrate, the apparatus comprising:
an electron source configured to generate electrons for an electron beam;
scanning deflectors configured to deflect the electron beam over the target area;
an objective lens for focusing the electron beam onto the target area;
a substrate holder for holding the substrate;
a detector configured to detect scattered electrons;
a controller configured to control the apparatus; and
computer-readable program code stored in computer-readable data storage accessible by the controller, wherein the computer-readable program code is configured to a) controllably scan an electron beam over the target area of the substrate and detect extracted secondary electrons during an imaging phase, b) increase an electric field at a surface of the substrate after the imaging phase, c) controllably scan the electron beam over the target area of the substrate during a charge control phase, and d) decrease the electric field at the surface of the substrate after the charge control phase, wherein the imaging and charge control phases alternate.

21. The apparatus of claim 20, wherein a voltage difference between the objective lens device and the substrate holder is changed by at least a magnitude of one hundred volts between imaging and charge control phases, and wherein a cycle including the imaging phase and the charge control phase is repeated at a frequency of at least fifteen hertz.

22. The apparatus of claim 20, wherein the substrate is controllably moved in a direction perpendicular to a scan direction so that the electron beam is scanned over swaths during the alternating imaging and charge control phases.

* * * * *